United States Patent [19]

Busse

[11] Patent Number: 4,557,607
[45] Date of Patent: Dec. 10, 1985

[54] METHOD AND DEVICE FOR STRUCTURAL, SUPERFICIAL AND DEEP ANALYSIS OF A BODY

[75] Inventor: Gerhard Busse, Sauerlach, Fed. Rep. of Germany

[73] Assignee: Carl-Zeiss-Stiftung, Heidenheim/Brenz, Oberkochen, Fed. Rep. of Germany

[21] Appl. No.: 632,278
[22] PCT Filed: Aug. 26, 1981
[86] PCT No.: PCT/DE81/00130
§ 371 Date: Apr. 12, 1982
§ 102(e) Date: Apr. 12, 1982
[87] PCT Pub. No.: WO82/00891
PCT Pub. Date: Mar. 18, 1982

Related U.S. Application Data

[63] Continuation of Ser. No. 371,300, Apr. 12, 1982, abandoned.

[30] Foreign Application Priority Data

Sep. 1, 1980 [DE] Fed. Rep. of Germany ....... 3034944

[51] Int. Cl.⁴ .............................................. G01J 5/00
[52] U.S. Cl. .................................... 374/121; 374/124; 374/130
[58] Field of Search ............... 290/341, 358.1, 334, 290/353; 374/121, 124, 130, 5, 7, 4, 43, 44; 73/606

[56] References Cited

U.S. PATENT DOCUMENTS

| | | | |
|---|---|---|---|
| 3,206,603 | 9/1965 | Mauro | 374/5 |
| 3,210,546 | 10/1965 | Perron | 374/5 |
| 3,287,556 | 11/1966 | Good | 250/353 |
| 3,681,970 | 8/1972 | Wells | 374/5 |
| 3,805,073 | 4/1974 | Jayachandra et al. | 250/353 |
| 3,808,439 | 4/1974 | Renius | 250/334 |
| 3,842,277 | 10/1974 | Jayachandra | 250/341 |
| 4,041,313 | 8/1977 | Potter et al. | 250/341 |
| 4,158,772 | 6/1979 | Reedy | 250/341 |
| 4,255,971 | 3/1981 | Rosencwaig | 73/606 |
| 4,267,732 | 5/1981 | Quate | 73/606 |

OTHER PUBLICATIONS

IBM Technical Disclosure Bulletin, vol. 19, No. 1, Jun. 1976 (New York, U.S.), K. Mueller u.a., 'Emission Spectrophotometer', see pp. 303-304.
Solid State Technology, vol. 18, No. 8, Aug. 1975, (New York, U.S.) H. Matare, 'Wafer Testing', pp. 58-62, see pp. 59-61 cited in the application.
Photoacoustic and Photothermal Spectroscopy, Svein Otto Kanstad & Phys. Technol., vol. II, 1980 (Gr. Britain), Per-Erik Nordal.
"Materials Evaluation", Thermal Surface Impedance Method for Nondestructive Testing by Green, Oct. 1967.
"Solid State Technology", Thermal-Wave Microscopy by Rosencwaig, Mar. 1982.
High Speed Thermal Image Transducer for Practical NDT Applications by Green, May 1970.
Depth-Profiling and Thickness Measurement by Rosencwaig 1980.

*Primary Examiner*—Charles Frankfort
*Assistant Examiner*—David R. Schuster
*Attorney, Agent, or Firm*—Hopgood, Calimafde, Kalil, Blaustein & Judlowe

[57] ABSTRACT

A method for the structural, superficial and deep analysis of a body is disclosed. The method includes scanning the body to be examined using a modulated excitation radiation beam so as to impart a thermal modulation to the body. The thermal modulation is then measured on the side of the body distal to the side exposed to the beam. The amplitude as well as the phase of the measured thermal modulation is used to determine the thickness and structure of the body. A device for accomplishing the above described method is also disclosed.

19 Claims, 5 Drawing Figures

METHOD AND DEVICE FOR STRUCTURAL, SUPERFICIAL AND DEEP ANALYSIS OF A BODY

BACKGROUND OF THE INVENTION

This application is a continuation of application Ser. No. 371,300, filed Apr. 12, 1982, now abandoned.

The present invention relates to a method and a device for the structural, superficial and deep analysis of a body.

For the monitoring of manufacture and the testing of workpieces it is frequently necessary to measure thicknesses of material and determine the superficial and inner structures, for instance, of internal holes or shrinkage cavities in solids.

In order to determine surface structures and check bodies of transparent material optical measuring and testing methods are employed. The examination of structures below the surface of the body as well as contact-free thickness measurements require a large expense when the test pieces consist of bodies of opaque material, for instance metal or a semiconductor. For such examinations ultrasonic or X-ray methods have been generally used up to now. The ultrasonic methods do not operate without contact and are therefore not suitable for the direct continuous examination of moving parts such as, for instance, the examination of rolled plates. Although X-ray methods do not require contact with the material, they are only of limited use, however, for the detection of interface structures.

Devices are also already known which operate in accordance with the so-called opto- (or photo-) acoustic method and which serve for the detection of material structures even below the surface of the material. In the opto-acoustical method local temperature modulation is produced on the surface of the solid to be examined by an intensity-modulated beam of light due to the periodic feeding of heat caused by absorption, said temperature modulation being dependent in amplitude and phase on the removal of heat within the solid.

If the solid is arranged in a hermetically closed chamber, its temperature modulation can be measured by a microphone arranged within the chamber. Since the temperature modulation of the solid goes hand-in-hand with a corresponding modulation of its extent, it can be measured also with a piezoelectric receiver which is firmly connected to the body to be examined. A photoacoustic microscope which operates in accordance with this principle is known from U.S. Pat. No. 4,255,971. This microscope serves to produce an image of the test piece which is displaced for this purpose with respect to the stationary beam of light.

In both known methods for the opto-acoustical production of a signal, structures within the body to be examined can be imaged via the phase of the measurement signal.

It can readily be seen that in the known methods for the production of an opto-acoustical measurement signal the actual measurement or imaging is limited to a very small range of depth limited by the depth of thermal penetration of the beam of light. The depth of thermal penetration in the case of a test piece of aluminum with a modulation frequency of the beam of light of 20 Hz is only 0.12 cm. Furthermore, these methods require physical contact between the receiver and the sample and are therefore limited to the measurement of small bodies.

BRIEF STATEMENT OF THE INVENTION

The object of the present invention is to provide an opto-acoustical method which permits structural analysis of surface and depth, even on bodies of large diameter and on moving parts, without the range of depth which can be covered being limited by the depth of thermal penetration of the modulated excitation beam.

Starting from the known method in which the body to be examined is scanned with a focused modulated excitation beam and the temperature modulation of the body which is locally induced thereby is measured, this object is achieved by measuring, on the side of the body facing away from the impinging excitation beam, the modulated infrared radiation which proceeds from it. Therefore, only the transmitted heat wave is detected. The signal produced by it is present as an alternating signal which can be electronically processed in simple fashion.

The excitation beam may consist of electromagnetic radiation, for instance light, of electrons or else of ions. In each case an electromagnetic or corpuscular radiation is used which is absorbed by the body to be examined. The detector which serves for the measurement of the infrared radiation transmitted by the body is so selected that it operates at the maximum of the Planck function. For a body of a temperature of 300° K. this is, for instance, about 9 $\mu$m. This wavelength will be smaller the hotter the specimen is.

The extent of the body to be examined in the direction of the excitation beam, i.e. the thickness of the material, is not limited by the depth of thermal penetration of the excitation beam in the method of the present invention. It may amount to several millimeters, for instance 7 or 8, depending on the power of the source of the excitation beam, the sensitivity of the infrared detector, the material of the specimen, and the required signal sensitivity.

For the practical uses of the method, particularly the testing of opaque materials such as metals and semi-conductors, there is a linear relationship between the phase angle of the measurement signal and the thickness of material as well as an exponential law for the dependence of the amplitude on the thickness of the material.

By utilization of the different dependencies to which phase and amplitude of the measurement signal are subject it is possible to distinguish between optical and thermal properties of the body to be examined. Since the phase as signal is produced from a transit-time delay, this measurement, in addition to its suitability for the determination of thickness, is also sensitive to interfaces so that, for instance, holes in metal parts can still be recognized even if they have been subsequently filled by the surrounding material.

The amplitude of the measurement signal is preferably used to examine structures of the body which are close to the surface. By use of the parallax effect of the heat waves proceeding from the body depth localization of structures is also possible. The parallax effect can be utilized both in the amplitude and in the phase-angle measurement.

It is particularly advantageous to position-modulate the excitation beam by a superimposed oscillating movement during its scanning movement over the body to be examined. This modulation may take place linearly, perpendicular or parallel to the scanning direction of the beam; however, it is also possible to conduct the excitation beam along an ellipse or a circle. With this type of modulation only signal changes along the direction of the oscillating movement are recorded. The component of the gradient of the signal which is parallel thereto is obtained. Upon circular modulation of the beam the alternating component of the signal found is proportional to the amount of the gradient.

The imaging contrasts of structures can thus be increased by the position-modulation described. By selection of the direction of oscillation structures extending perpendicular to this direction can be emphasized particularly clearly.

DETAILED DESCRIPTION

The invention will be explained in further detail below with reference to FIGS. 1 to 5 of the accompanying drawings in which.

Figure 1:
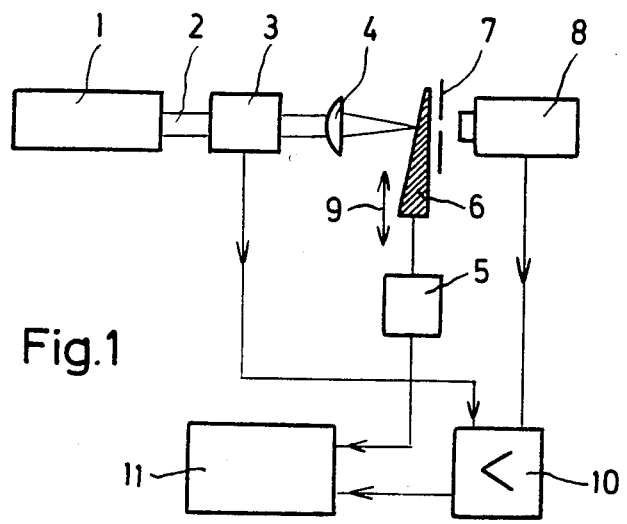
FIG. 1 shows an illustrative embodiment of a device for measuring thickness by the method of the invention.

In the device shown in FIG. 1, the scanning beam 2 produced by a laser 1 is modulated in intensity by a chopper 3 and focused by a diagrammatically indicated lens system 4 onto the surface of a test piece 6. The latter can be displaced laterally in the direction indicated by the arrow 9 by means of a transport device 5. The test piece 6 shown here is, for instance, an aluminum wedge used for calibration purposes in thickness measurements. An image-limiting stop 7 is arranged behind the test piece 6. The infrared radiation which passes through it falls upon an infrared detector 8 whose signal is fed to a lock-in amplifier 10 having a synchronizing connection to the chopper 3. From the amplifier 10 the measurement signal passes to an indicating unit 11 to which a signal proportional to the path of displacement of the test piece 6 is fed from the transport device 5. The indicating unit 11 thus produces a curve which shows the dependence of the measurement signal on the locus of the test piece 6.

In the embodiment shown in FIG. 1 a laser 1 is the source for the excitation beam 2. It can be developed, for instance, as an argon-ion laser which produces a beam 2 which before focusing contains a power of 50 mW. The focusing action of lens system 4 produces a power density of about $10^6$ to $10^8$ W/cm$^2$ at the point of impingement of the beam on the test piece 6. This power is sufficient to effect, for instance, on an aluminum test piece 6 measurements which extend to a depth of up to 7 or 8 mm.

Figure 2:
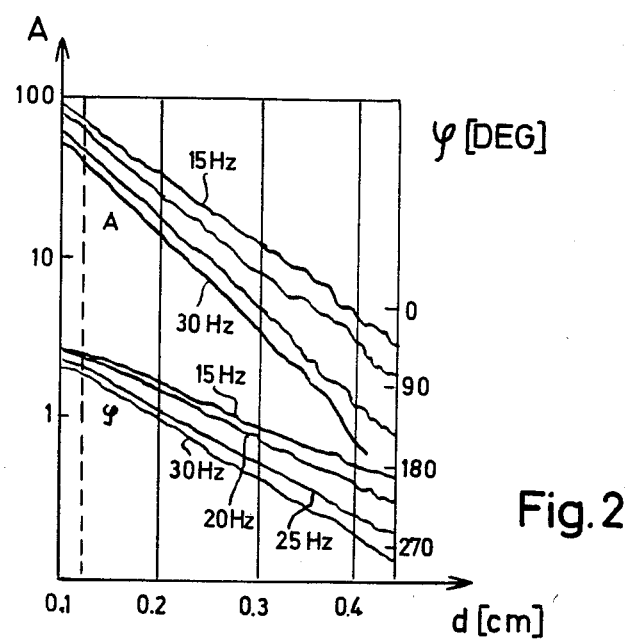
FIG. 2 shows curves which indicate the dependence of amplitude and phase of the measurement signal on the thickness of the body to be measured.

With the device shown in FIG. 1 the calibration curves of FIG. 2 can be obtained; these curves show the dependence of the amplitude A and of the phase angle $\phi$ on the thickness d of the body 6 for different modulation frequencies of the beam 2.

The device of FIG. 1 can be developed in such a manner that both the amplitude A and the phase angle $\phi$ of the heat radiation passing through the test piece 6 can be measured. From these measurements the thickness of the test piece 6 can be determined on basis of the calibration curves of FIG. 2. The test piece may consist of an opaque material, for instance of metal or a semiconductor. The test piece 6 may also be a biological specimen.

If a body of known thickness is used in the device of FIG. 1 instead of the test piece 6, the power of the laser 1 can be determined in a simple unambiguous manner by means of the signal produced by the receiver 8.

As infrared detector 8 practically all known detectors can be used. Measurement is effected at the maximum of the Planck function which is about 9 $\mu$m when the test piece 6 is at room temperature. Golay cells, bolometers or else Hg-Cd-Te detectors can be used as possible infrared detectors.

Figure 3:
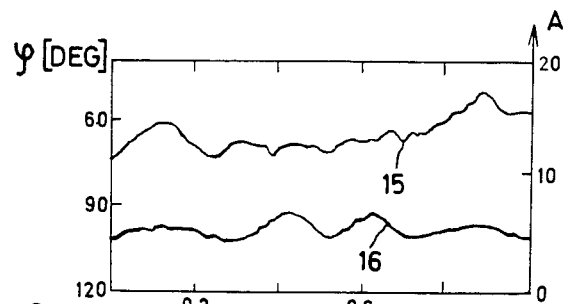
FIG. 3 is a composite of two diagrams (a and b) positioned for correlation as a function of the coordinate x, FIG. 3a being an enlarged fragmentary thickness section of a given body to be measured by the device of FIG. 1, and FIG. 3b being a graphical display of measurement curves for said fragmentary section.

FIG. 3a shows a test body 12 which consists, for instance, of metal and contains within it two parallel voids or ducts 13. The body surface which faces the excitation beam 2 is variously covered at individual places by a layer of graphite 14. If this body is moved through the scanning beam 2 instead of the wedge-shaped testpiece 6 shown in FIG. 1, then the curve 15 of FIG. 3b is obtained if the receiver part is developed in such a manner that the indicating unit 11 indicates the amplitude of the measurement signal. If the device is developed in such a manner that the indicating unit 11 shows the phase angle $\phi$ then the curve 16 is obtained.

Curve 15 shows that the amplitude responds essentially to the surface structures of the test piece 12 while the structures within the test piece are represented practically solely by the phase angle $\phi$ in curve 16. It is therefore advisable to use the phase angle $\phi$ for the measurement of internal structures within a body.

Figure 4:
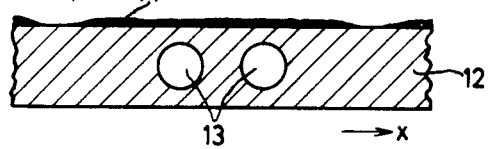
FIG. 4 shows an illustrative embodiment of a device for producing a microscopic image of a body.
Figure 4:
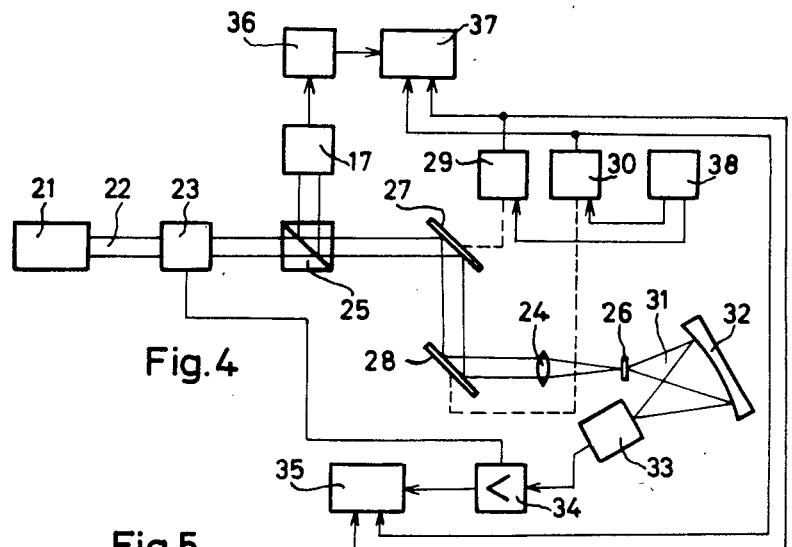

In the embodiment shown in FIG. 4, the beam 22 produced by a laser 21 is modulated in intensity by means of a chopper 23 and passes via mirrors 27 and 28 to an optical system 24, shown diagrammatically, which focuses the beam 22 on the surface of a test piece 26, fixed in space. The mirrors 27 and 28 are so moved via deflection units 29 and 30 that the excitation beam 22 scans a predetermined surface region of the test piece 26 in meander form.

Within the illumination ray path there is provided a beam splitter 25 which feeds the light reflected by the surface of the test piece 26 to an observation unit 17. The latter may be, for instance, a telescope so that an observer can continuously observe the place of impingement of the excitation beam 22 on the workpiece 26.

Thermal infrared radiation 31 given off by the heat wave transmitted through the test piece 26 is focused via a concave mirror 32 onto a receiver 33. Practically all known infrared detectors can once again be used here. The signal produced by the receiver 33 is fed to a lock-in amplifier 34 which feeds the demodulated signal to an indicating unit 35. Signals which are proportional to the deflections of the mirrors 27 and 28 are fed to said unit by units 29 and 30. In this way it is possible to display a microscopic image of the sample 26 by means of an indicating unit 35.

If the amplitude of the infrared radiation 31 is used for the display, then the indicating unit 35 shows a structural image of the regions of the test piece 26 which are close to the surface. On the other hand, if the phase angle 4 is used for the display, a structural image within the deeper regions of the test piece 26 is obtained.

It is possible to develop the observation unit 26 (sic) within the illumination ray path in such manner that a detector, for instance a photomultiplier 36, is connected behind it. The signal produced by the photomultiplier is fed to an indicating unit 37 to which the deflection voltages of the units 29 and 30 are also fed.

The indicating unit 37 thus displays an optical image of the surface of the test piece 26 which, for instance for purposes of orientation, can be superimposed on the display of the indicating unit 35.

The device shown in FIG. 4 is used to particular advantage for the examination of integrated circuits or corresponding semiconductor structures. In order in such case to obtain a clearer picture of structures within the test piece 26 it is advisable to display only the gradient of the measurement signal. For this purpose, a deflection signal which is superimposed on the deflection units 29 and 30 is produced via an arrangement 38. By means of this superimposed deflection voltage, an oscillating movement which extends essentially perpendicular to the direction of propagation is superimposed, for instance, on the scanning movement of the beam 2 in one coordinate direction, as shown by way of example in FIG. 5b. If the arrangement 38 produces two deflection signals which are substantially sinusoidal and have a phase difference of 90° then a circular oscillation movement is superimposed on the scanning movement of the beam 22 so as to produce a scanning track such as shown, for instance, in FIG. 5a. It is also possible, an in many cases advantageous, to make the two sinusoidal voltages of the arrangement 38 of different amplitude so that an elliptical oscillation of the scanning beam 2 is obtained.

Figure 5:
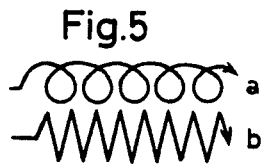
FIG. 5 is an enlarged presentation of two scanning paths of the excitation beam upon the position-modulation thereof.

Measurements with a device of the type shown in FIG. 5 have given a position resolution of the structural image of about 2 μm.

Upon position modulation of the beam 22, intensity modulation by means of the chopper 22 (sic) is normally dispensed with. However, in certain cases it may be advantageous to combine the two modulations in order, for instance, to obtain depth information.

Upon position modulation of the beam 22, a contrasted microscope image is obtained on the indicating unit 35 which image can be used for rapid analyses or else for automating structure recognitions.

The method of the invention finds particularly advantageous use in the FIG. 4 device when testing weld seams on thin sheets for strinkage holes and inclusions. Such weld seams are to be tested, for instance, in the case of pacemakers in which sheets of a thickness of 2 to 5/10 mm are used. The testing of such weld seams was up to now not possible for all practical purposes since both analysis with ultrasonics and with X-rays fails to give usable information. Such information is, however, obtained in dependable manner with the method of the present invention.

The method of the present invention substantially broadens the previously known opto-acoustical methods since for the first time it makes possible contact-free measurement and/or imaging even of larger areas without the otherwise disturbing limited depth effect.

Other advantageous embodiments of the opto-acoustical methods which differ predominantly by the nature of the obtaining of the signal are also possible. It is possible, for instance, in the case of specimens of insulating material, for instance biological specimens, to measure the dielectric constant with a high frequency bridge and further use this signal. Conductive specimens can also be examined by measuring their conductivity. It is also possible in an opto-acoustical method to use a pyroelectrical receiver for the production of the signal or to utilize pyroelectrical effects of the sample itself. Phase transitions of the specimen can also be used for the signal detection.

I claim:

1. The method of analyzing a body for its surface structure and for its subsurface structure, wherein the body has two opposed surfaces, which method comprises using a cyclically modulated and focused excitation beam to impinge upon and to scan one surface of the body, the focused beam having sufficient intensity to locally induce a thermal modulation within the body and to produce a modulated infrared emanation from the outer surface of the body, measuring amplitude of the modulated infrared emanation in order to obtain an indication of the character of surface structure, and measuring phase shift of the modulated infrared emanation with respect to the modulation cycle of the focused beam in order to obtain an indication of subsurface structure, each of the measurements being as a function of scan displacement.

2. A method for the structural, superficial and deep analysis of a body wherein the body has two opposed surfaces, which method comprises using a cyclically modulated and focused excitation beam to impinge at a spot upon and to scan one surface of the body, the focused beam having sufficient intensity to locally induce a thermal modulation within the body and to produce a modulated infrared emanation from the other surface of the body, and measuring the modulated infrared emanation synchronously with the cyclical modulation and as a function of scan displacement to obtain at least the phase difference between the impinging and emanating modulations whereby surface and/or subsurface structural character may be ascertained from the measurement.

3. The method of claim 2, wherein the other-surface area from which the emanation measurements are made is larger than the local area of beam focus on the one surface.

4. The method of claim 2, wherein the measurement of the modulated infrared radiation is effected at the maximum of the Planck function.

5. The method of claim 2, wherein the modulation of the excitation beam is a chopped modulation.

6. The method of claim 2, wherein the modulation of the excitation beam is a scan-induced modulation.

7. The method of claim 6, wherein the scan-induced modulation is the result of two-dimensional displacement of the focus spot and of the body with respect to each other.

8. The method of claim 7, wherein the two-dimensional displacement includes a circular component.

9. The method of claim 2, wherein amplitude of the modulated infrared emanation is measured in an analysis of the surface structure of the body.

10. The method of claim 2, wherein the phase difference between the beam modulation and the modulation of the infrared emanation is measured in a deep analysis of the structure of the body.

11. A device for the structural, superficial and deep analysis of a body comprising a source for generating a focused cyclically modulated excitation beam, the focused beam having sufficient intensity upon impingement with the body being examined to produce a thermal modulation in the body and to produce a modulated infrared emanation from the side distal to the side upon which the excitation beam impinges; and infrared-detector means including an amplifier for detecting the modulated infrared emanation, said detector means being positioned at offset from the distal side of the body, and said amplifier having a synchronizing connection to said source, for obtaining at least the phase difference between the impinging and emanating modulations.

12. The device of claim 11, in which said detector amplifier having said synchronizing connection is responsive directly to the modulation frequency of the excitation beam of said source.

13. The device of claim 11, wherein two movable mirrors are positioned in the path of the excitation beam for scanning the body in a rectangular-coordinate system and wherein said infrared detector is connected to means for displaying the modulated infrared radiation as a function of the body coordinates.

14. The device of claim 13, wherein the two mirrors are connected to second means for producing linear-deflection signals and to third means for producing position-modulation signals.

15. The device of claim 13, further including a beam splitter positioned in the scanning beam path and a photo detector connected to an image-producing device for observing the surface structure of the body to be examined, said photo detector and image-producing device being arranged in the path of the beam split off by said beam splitter.

16. The device of claim 11, wherein an image-limiting stop is positioned between the infrared detector and the body examined.

17. The device of claim 13, further including a beam splitter positioned in the path of the scanning beam, and telescope means positioned in the path of the portion of the beam split off by the beam splitter, said beam splitter and said telescope means being adapted to monitor the point of impingement of the scanning beam on the surface of the body.

18. The method of testing weld seams on thin metal sheets, wherein the weld-seam region defines a body with two opposed surfaces, which method comprises using a cyclically modulated and focused excitation beam to impinge upon and to scan one surface of the weld-seam region, the focused beam having sufficient intensity to locally induce a thermal modulation within the weld-seam region and to produce a modulated infrared emanation from the other of the body, and measuring the modulated infrared emanation synchronously with the cyclical modulation and as a function of scan displacement to obtain at least the phase difference between the impinging and emanating modulations, whereby surface and/or subsurface structural character may be ascertained from the measurement.

19. The method of examining a semi-conductor body region having two opposed surfaces, which method comprises using a cylically modulated and focused excitation beam to impinge upon and to scan one surface of the region, the focused beam having sufficient intensity to locally induce a thermal modulation within the region and to produce a modulated infrared emanation from the other surface of the body region, and measuring the modulated infrared emanation synchronously with the cyclical modulation and as a function of scan displacement to obtain at least the phase difference between the impinging and emanating modulations, whereby surface and/or subsurface structural character may be asceratained from the measurement.

* * * * *